(12) United States Patent
Gogotsi et al.

(10) Patent No.: US 8,119,021 B2
(45) Date of Patent: Feb. 21, 2012

(54) FUNCTIONAL NANOPARTICLE FILLED CARBON NANOTUBES AND METHODS OF THEIR PRODUCTION

(75) Inventors: Yury Gogotsi, Ivyland, PA (US);
Guzeliya Korneva, Plainsboro, NJ (US);
Gennady Friedman, Richboro, PA (US)

(73) Assignee: Drexel University, Philadelphia, PA (US)

( * ) Notice: Subject to any disclaimer, the term of this patent is extended or adjusted under 35 U.S.C. 154(b) by 894 days.

(21) Appl. No.: 11/910,689

(22) PCT Filed: Apr. 6, 2006

(86) PCT No.: PCT/US2006/013215
§ 371 (c)(1),
(2), (4) Date: May 6, 2008

(87) PCT Pub. No.: WO2006/113192
PCT Pub. Date: Oct. 26, 2006

(65) Prior Publication Data
US 2009/0202644 A1    Aug. 13, 2009

Related U.S. Application Data

(60) Provisional application No. 60/668,636, filed on Apr. 6, 2005.

(51) Int. Cl.
*C04B 35/00* (2006.01)
*C09D 5/23* (2006.01)
*H01F 1/00* (2006.01)
(52) U.S. Cl. .............................................. 252/62.51 R
(58) Field of Classification Search .................. None
See application file for complete search history.

(56) References Cited

U.S. PATENT DOCUMENTS

| | | | |
|---|---|---|---|
| 4,663,230 | A | 5/1987 | Tennent |
| 5,346,683 | A | 9/1994 | Green et al. |
| 5,424,054 | A | 6/1995 | Bethune et al. |
| 5,457,343 | A | 10/1995 | Ajayan et al. |
| 5,543,378 | A | 8/1996 | Wang |
| 5,547,748 | A | 8/1996 | Ruoff et al. |
| 5,580,612 | A | 12/1996 | Hickel et al. |
| 6,090,363 | A | 7/2000 | Green et al. |
| 6,129,901 | A | 10/2000 | Moskovits et al. |
| 6,139,919 | A | 10/2000 | Eklund et al. |
| 6,277,318 | B1 | 8/2001 | Bower et al. |
| 6,544,463 | B1 | 4/2003 | Luzzi et al. |
| 6,683,783 | B1 | 1/2004 | Smalley et al. |

(Continued)

FOREIGN PATENT DOCUMENTS

WO    WO 01/08164 A1    2/2001

(Continued)

OTHER PUBLICATIONS

Kyotani et al(Synthesis of Carbon Nanotube Composites in Nanochannels of an anodic Aluminum Oxide Film, Bull. Chem. Soc. Jpn., (1999), 72, 1957-1970).*

(Continued)

*Primary Examiner* — Emily M Le
*Assistant Examiner* — Michael Forrest
(74) *Attorney, Agent, or Firm* — Woodcock Washburn, LLP

(57) ABSTRACT

Carbon nanotubes filled with a suspension or colloidal solution of functional nanoparticles and methods for production of carbon nanotubes loaded with functional nanoparticles are provided.

8 Claims, 7 Drawing Sheets

U.S. PATENT DOCUMENTS

2001/0051367 A1    12/2001    Kiang
2002/0027819 A1    3/2002    Tomanek et al.

FOREIGN PATENT DOCUMENTS

| | | |
|---|---|---|
| WO | WO 02/24572 A1 | 3/2002 |
| WO | WO 02/24573 A1 | 3/2002 |
| WO | WO 02/24574 A1 | 3/2002 |
| WO | WO 02/30816 A1 | 4/2002 |

OTHER PUBLICATIONS

Korneva et al(Carbon Nanotubes Loaded with Magnetic Particles, Nano Letters, 2005, vol. 5., No. 5., 879-884 first published on the web Mar. 30, 2005).*

Ajayan, P.M., et al., "Opening carbon nanotubes with oxygen and implications for filing," Nature, 1993, 362, p. 522-1096.

Ajayan, P.M., et al., "Capillarity-induced filling of carbon nanotubes," Nature, 1993, 361, 333-334.

Ajayan, P.M., et al., "Carbon nanotubes as removable templates for metal oxide nanocomposites and nanostructures," Nature, 1995, 375, 564-567.

Ajayan, P.M., et al., "Growth morphologies during cobalt-catailyzed single-shell carbon nanotube synthesis," Chem. Physics Ltrs., 1993, 215(3), 509-517.

Akasaka, T., et al., "$^{13}$C and $^{139}$La NMR studies of $La_2@C_{80}$: first evidence for circular motion of metal atoms in endohedral dimetallofullerenes," Angew. Chem. Int. Ed. Engl., 1997, 36(15), 1643-1645.

Akasaka, T., et al., "Synthesis of the first adducts of the dimetallofullerenes $La_2@C_{80}$ and $Sc_2@C_{84}$ by addition of a disilirane," Angew. Chem. Int. Ed. Engl., 1995, 34(19), 2139-2141.

Alvarez, M.M., et al., "$La_2C_{80}$ A soluble dimetallofullerene," Phys. Chem., 1991, 95, 10561-10563.

Bandow, S., et al., "Truning peapods into double-walled carbon nanotubes," MRS Bulletin, 2004, 260-264.

Berber, S., "Microscopic formation mechanism of nanotube peapods," Am. Physical Society, 2002, 185502-1-185502-4.

Bethune, D.S., et al., "Cobalt-catalysed growth of carbon nanotubes with single-atomic-layer walls," Nature, 1993, 363, 605-606.

C&EN, Science/Technology, "Another nanotube surprise: Buckypeas in a pod," Jan. 11, 1999, p. 32.

Chen, Y.K., et al., "Synthesis of carbon nanotubes containing metal oxides and metals of the d-block and f-block transition metals and related studies," J. Mater. Chem., 1997, 7(3), 545-549.

Chen, G., et al., "Chemically doped double-walled carbon nanotubes: cylindrical molecular capacitors," Am. Physical Soc., 2003, 90(25), 257403-1-257403-4.

Chikkannanavar, S.B., et al., "Processing of single wall carbon nanotubes and implications for filing experiments," Mat. Res. Soc. Symp. Proc., 2002, 706, Z2.7.1-Z2.7.6.

Cho, Y., et al., "Orbital hybridization and charge transfer in carbon nanopeapods," Am. Phys. Soc., 2003, 106402-1-106402-4.

Davis, J.J., et al., "The immobilisation of proteins in carbon nanotubes," Inorganica Chimica Acta, 1998, 272, 261-266.

Dresselhaus, M.S., et al., "Carbon nanotubes: continued innovations and challenges," MRS Bulletin, 2004, 237-243.

Dujardin, E., et al., "Capillarity and wetting of carbon nanotubes," Science, 1994, 265, 1850-1852.

Eisberg, R., et al., Quantum Physics of Atoms, Molecules, Solids, Nuclei, and Particles, Solids-conductors and Semiconductors, John Wiley & Sons (Eds.), New York, 1985, Chapter 13, p. 444.

Eto, Y., et al., "Introduction of JWS-2000 review SEM," JEOL News, 2004, 39(2), 13-15.

Han, S., "charge transfer and gap states in semiconducting nanopeapods: a theoretical study," J. of the Korean Phys. Soc., 2004, 894-898.

Heiney, P.A., "Structure, dynamics and ordering transition of solid $C_{60}$," J. Phys. Chem. Solids, 1992, 53(11), 1333-1352.

Hino, S., et al., "Photoelectron spectra of metallofullerenes, $GdC_{82}$ and $La_2C_{80}$: electron transfer from the metal to the cage," Chem. Phys. Lett., 1997, 281, 115-122.

Iijima, S., et al., "Single-shell carbon nanotubes of 1-nm diameter," Nature, 1993, 363, 603-604.

Iijima, S., "Helical microtubules of granphitic carbon," Nature, 1991, 354, 56-58.

Iijima, S., "Carbon nanotubes: past, present, and future," Physica B, 2002, 323, 1-5.

"Inside Illinois," Jan. 2002, 21(12), 1-12.

JEOL Ltd., Introduction of Products, JEOL News, http://www.jeol.co.jp/, 2004, 39(2), 26-27.

Kataura, H., et al., "Optical properties of fullerene-peapods," Proceeding of ISNM, 2001 to be published in AIP proceedings, 4 pages.

Kim, Y.-H., et al., "Dynamics of fullerene coalescence," arXiv:cond-mat/0211059v2, 2004, 1-4.

Kobayashi, K., et al., "A theoretical study of $C_{80}$ and $La_2@C_{80}$," Chem. Phys. Lett., 1995, 245, 230-236.

Kobayashi, K., et al., "Endohedral dimetallofullerenes $Sc_2@C_{84}$ and $La_2@C_{80}$. Are the metal atoms still inside the fullerene cages?," Chem. Phys. Lett., 1996, 261, 502-506.

Kwon, Y.-K. et al., "Bucky Shuttle" Memory Device: Synthetic Approach and Molecular Dynamics Simulations, Physical Review Letters: The American Physical Society, 1999, 82(7), 1470-1473.

Lee, J., et al., "Bandgap modulation of carbon nanotubes by encapsulated metallofullerenes," Nature, 2002, 415, 1005-1008.

Liu, J., et al., "Fullerene pipes," Science, 1998, 280, 1253-1256.

Maniwa, Y., et al., "$C_{70}$ molecular stumbling inside single-walled carbon nanotubes," in press (J. Phys. Soc. Jpn.), received Aug. 27, 2002, 1-13.

Matthews, C.K., et al., "Vaporization studies of buckminsterfullerene," J. Phys. Chem., 1992, 96, p. 3566-3568.

Mickelson, W., et al., "Packing $C_{60}$ in boron nitride nanotubes," Science, 2003, 300, 467-469.

Monthioux, M., et al., "Sensitivity of single-wall carbon nanotubes to chemical processing: an electron microscopy investigation," Carbon, 2001, 1251-1272.

Nakao, K., et al., "Ab initio molecular-orbital calculation for $C_{70}$ and seven isomers of $C_{80}$," Physical Review B, 1994, 49(16), 11 415-11 420.

Nikolaev, P., et al., "Diameter doubling of single-wall nanotubes," Chem. Phys. Lett., 1997, 266, 422-426.

Ohno, Y., et al., "Synthesis of carbon nanotube peapods directly on Si substrates," Applied Physics Letts., 2005, 86, 023109-1-023109-3.

Okazaki, T., et al., "Fullerenes and carbon nanotubes: nanocarbon assuming a leading role in the $21^{st}$ century," JEOL News, 2004, 39(2), 20-25.

Oshima, Y., "A study of metal nanowire structures by high-resolution transmission electron microscopy," JEOL News, 2004, 39(2), 8-12.

Qian, D., "Mechanics of $C_{60}$ in nanotubes," J. Phys. Chem. B, 2001, 105, 10753-10758.

Rao, A.M., et al., "Photoinduced polymerization of solid $C_{60}$ films," Science, 1993, 259, 955-957.

Rinzler, A.G., et al., "Large scale purification of single wall carbon nanotubes: process, product and characterization," Appl. Phys. A, 1998, 67, 29-37.

Saito, S., et al., "Design of carbon-nanotube based materials," Paper presented at Nanotubes 99, East Lansing, MI, USA, 1999, 4 pages.

Sato, W., et al., "Molecular and intramolecular dynamics of a $C_{80}$ dimetallofullerene," Phys. Rev. B, 1998, 58(16), 10 850-10 856.

Sloan, J., et al., "The size distribution, imaging and obstructing properties of $C_{60}$ and higher fullerenes formed within arc-grown single walled carbon nanotubes," Chem. Phys. Lett., 2000, 316, 191-198.

Sloan, J., et al., "Selective deposition of $UCI_4$ and $(KCI)_x(UCI4)_y$ inside carbon nanotubes using eutectic and noneutectic mixtures of $UCI_4$ and KCI," J. Solid State Chem., 1998, 140, 83-90.

Sloan, J., et al., "Imaging and characterization of molecules and one-dimensional crystals formed within carbon nanotubes," MRS Bulletin, 2004, 265-271.

Smith, D.W., et al., "Tumbling atoms and evidence for charge transfer in $La_2@C_{80}$SWNT," Chemical Physics Letters, 2000, 331, 137-142.

Smith, D.W., et al., "High-yield synthesis and one-dimensional structure of $C_{60}$ encapsulated in single wall carbon nanotubes," J. Appl. Phys., 2002, 91, 1-25.

Smith, D.W., et al., "Structural anisotropy of magnetically aligned single wall carbon nanotube films," Applied Physics Letters, Jul. 31, 2000, 77(5), 663-665.

Smith, D.W., et al., "Electron irradiation effects in single wall carbon nanotubes," Journal of Applied Physics, Oct. 1, 2001, 90(7), 3509-3515.

Smith, B.W., et al., "Carbon nanotube encapsulated fullerenes: a unique class of hybrid materials," Chem. Phys. Lett., 1999, 315, 31-36.

Suzuki, T., et al., "Electrochemistry and Ab initio study of the dimetallofullerene $La_2@C_{80}$," Angew. Chem. Int. Ed. Engl., 1995, 34(10), 1094-1096.

Thess, A., et al., "Crystalline ropes of metallic carbon nanotubes," Science, 1996, 273, 483-487.

Tsang, S.C., et al., "Thinning and opening of carbon nanotubes by oxidation using carbon dioxide," Nature, 1993, 362(8), p. 520-521.

Tsang, S.C., et al., "A simple chemical method of opening and filling carbon nanotubes," Nature, 1994, 372(10), 159-162.

Tsuji, K., "Grazing-exit electron probe microanalysis (GE-EPMA)," JEOL News, 2004, 39(2), 16-19.

Ugarte, D., et al., "Filling carbon nanotubes," Appl. Phys. A, 1998, 67, 101-105.

Vavro, J., et al., "Electrical and thermal properties of $C_{60}$-filled single-wall carbon nanotubes," Applied Physics Letts., 2002, 80(8), 1450-1452.

Wang, G.W., et al., "Synthesis and x-ray structure of dumb-bell-shaped $C_{120}$," Nature, 1997, 387, 583-586.

Yang, Q., et al., "Inner-tubular physicochemical processes of carbon nanotubes," Chinese Sci. Bulletin, 2003, 48(22), 2395-2403.

Yao, N., et al., "Young's modulus of single-walled carbon nanotubes," J. Appl. Phys., 1998, 84(4), 1939-1943.

Ye, H., et al., "TEM study of water in carbon nanotubes," JEOL News, 2004, 39(2), 2-7.

Yeretzian, C., et al., "Collisional probes and possible structures of $La_2C_{80}$," Chem. Phys. Lett., 1992, 196(3,4), 337-342.

Yoon, M., et al., "Energetics and packing of fullerenes in nanotube peapods," Physics & Astronomy Dept., Michigan State University, 2004, 1-4.

Zettl, A., et al., "Boron nitride nanotube peapods," Am. Institute of Physics, 2002, 140-144.

Zhang, B.L., et al., "Tight-binding molecular-dynamics simulation of buckyball collisioas," J. Phys. Chem., 1993, 97, p. 3134-3138.

Zhang, Y., et al., "Defects in arc-discharge-produced single-walled carbon nanotubes," Philos. Mag. Lett., 1999, 79(7), 473-479.

Zhang, B.L., et al., "The geometry of large fullerene cages: $C_{72}$ to $C_{102}$," J. Phys. Chem., 1993, 98(4), 3095-3102.

Zhao, Y., et al., "Dynamic topology of fullerene coalescence," Am. Physicol Soc., 2002, 88(18), 185501-1-185501-4.

Ajayan, P.M. et al., "Capillarity-induced Filling of Carbon Nanotubes," Nature, 1993, 361, 333-334.

Bakajin et al., "Separation of 100-Kilobase DNA Molecules in 10 Seconds," Analytical Chemistry, 2001, 73, 6053-6056.

Baughman et al., "Carbon Nanotubes—The Route Toward Applications," Science, 2002, 297, 787-792.

Bradley et al., "Nanotubes Synthesis Using Alumina Template," Chemistry Preprint Archive, 2002, 237-242.

Bradley et al., "Bipolar Electrodeposition of Polypyrrole onto both ends of a Carbon Nanotube," Chemistry Preprint Archive, 2003, 3, 245-250.

Brochard, F. et al., "Theory of Magnetic Suspensions in Liquid Crystals," Journal de Physique, 1970, 31, 691-708.

Cao et al., "Gradient Nanostructures for Interfacing Microfluidics and Nanofluidics," Applied Physics Letters, 2002, 81, 3058-3060.

Coey, J.M.D. et al., "The Magnetism of Carbon," Physics World, 2004.

Doyle et al., "Self-Assembled Magnetic Matrices for DNA Separation Chips," Science, 2002, 295, 2237.

Dujardin et al., "Capillarity and Wetting of Carbon Nanotubes," Science, 1994, 265, 1850-1852.

Gao et al., "Carbon Nanotubes Filled with Metallic Nanowires," Carbon, 2004, 42, 47-52.

Gogotsi, Y., "How Safe are Nanotubes and other Nanofilaments," Materials Research Innovations, 2003, 7, 192-194.

Henriquez et al., "The Resurgence of Coulter Counting for Analyzing Nanoscale Objects," Analyst, 2004, 129, 478-482.

Karnis, A. et al., "The Flow of Suspensions Through Tubes," Journal of Colloid and Interface Science, 1967, 23, 120.

Kornev, K.G. et al., "Modeling of Spontaneous Penetration of Viscoelastic Fluids and Biofluids into Capillaries," Journal of Colloid Interface Science, 2003, 262, 253-262.

Lin et al., "Advances Toward Bioapplications of Carbon Nanotubes," Journal of Materials Chemistry, 2004, 14, 527-541.

Minc, N. et al., "Quantitative Microfluidic Separation of DNA in Self-Assembled Magnetic Matrixes," Analytical Chemistry, 2004, 76, 3770-3776.

Naguib et al., "Filling and Chemical Modification of Carbon Nanotubes with Polymers," Abstracts of Papers of the American Chemical Society Annual Meeting 2003, 226:U535.

Nikitin et al., "The Magnetic, Elastic, Structural, and Magnetodeformational Properties of Magnetoelastics," Polymer Science Series A, 2004, 46(3), 498-509.

Rossi et al., "Environmental Scanning Electron Microscopy Study of Water in Carbon Nanopipes," Nano Letters, 2004, 4, 989-993.

Singh, M. K. et al., "Ni and Ni/Pt Filling Inside Multiwalled Carbon Nanotubes," Journal of Nanoscience and Nanotechnology, 2003, 3, 165-170.

Tolles, W.M. et al., "Nanotechnology, a stimulus for Innovation," Current Science, 2003, 85, 1746-1759.

Ugarte et al., "Nanocapillarity and Chemistry in Carbon Nanotubes," Science, 1996, 274, 1897-1899.

Wu et al., "Transparent, Conductive Carbon Nanotube Films," Science, 2004, 305, 1273-1276.

Ye et al., "Wall Structure and Surface Chemistry of Hydrothermal Carbon Nanofibres," Nanotechnology, 2004, 15, 232-236.

Yoshida et al., "Improvement of MFM tips using Fe-Alloy-Caped Carbon Nanotubes," Physica B-Condensed Matter, 2002, 323, 149-150.

Zrinyi et al., "Kinetics of the Shape Change of Magnetic Field Sensitive Polymer Gels," Polymer Gels and Networks, 1998, 6, 441-454.

Kyotani, T. et al., "Formation of Ultrafine Carbon Tubes by Using an Anodic Aluminum Oxide Film as a Template," Chemistry of Materials, Aug. 1995, 7(8), 1427-1428.

Tsang, S.C. et al., "A simple chemical method of opening and filling carbon nanotubes," Nature, Nov. 10, 1994, 372, 159-162.

\* cited by examiner

FUNCTIONAL NANOPARTICLE FILLED CARBON NANOTUBES AND METHODS OF THEIR PRODUCTION

CROSS-REFERENCE TO RELATED APPLICATIONS

This application is the National Stage of International Application No. PCT/US2006/013215 filed Apr. 6, 2006, which claims the benefit of U.S. Provisional Application No. 60/668,636, filed Apr. 6, 2005, the disclosure of which is incorporated herein by reference in its entirety.

This patent application claims the benefit of priority to U.S. Provisional Application Ser. No. 60/668,636, filed Apr. 6, 2005, the teachings of which are herein incorporated by reference in their entirety.

FIELD OF THE INVENTION

The present invention provides carbon nanotubes (CNTs) filled with a suspension or colloidal solution of functional nanoparticles. The present invention also provides methods for production of CNTs loaded with functional nanoparticles. In one embodiment, CNTs filled with magnetic nanoparticles and methods for their production are provided. In other embodiments CNTs filled with gold colloidal nanoparticles and nanodiamonds are described.

BACKGROUND OF THE INVENTION

The unique physico-chemical properties of carbon nanotubes (CNTs) has initiated extensive research into their possible applications in various areas of engineering (Baughman et al. *Science* 2002 297, 787-792; Rossi et al. *Nano Letters* 2004 4, 989-993; Tolles, W. M. and Rath, B. B. *Current Science* 2003 85, 1746-1759; Gogotsi, Y. *Materials Research Innovations* 2003 7, 192-194; Lin et al. *Journal of Materials Chemistry* 2004 14, 527-541).

The unique conductive properties of CNTs have attracted engineers to investigate methods to make CNTs magnetic as well (Gao et al. Carbon 2004 42:47-52; Coey, J. M. D. and Sanvito, S. Physics World 2004). To the best of the inventors' knowledge, previous attempts have had limited success. For example, nanotubes with magnetic particles imbedded into CNTs during synthesis do not have useful magnetic properties. Further, the amount and location of the magnetic material inside the tube is difficult to control.

Techniques disclosed thus far for producing magnetic needles, are expensive, time-consuming (Singh et al. Journal of Nanoscience and Nanotechnology 2003 3:165-170), and have a relatively low yield. When increasing magnetization of magnetic needles, it is also important to prevent nanoneedles from agglomeration when magnetic field is not applied. Thus, encapsulating paramagnetic particles into CNT is desirable as it makes magnetic needles stable.

The phenomenon of spontaneous penetration of fluids into wettable capillaries has been taken as a guiding idea to load nanotubes with magnetic nanoparticles. As known from everyday experience, when a capillary is set in contact with a wetting fluid, the fluid spontaneously penetrates inside. This method of filling of nanotubes with molten metals has been suggested (Ajayan, P. M. and Iijima, S. Nature 1993 361:333-334; Dujardin et al. Science 1994 265:1850-1852; Ugarte et al. Science 1996 Science 274:1897-1899). Drawbacks of using the melts in this manner, however, include time consumption in that such methods are quite tedious and include the unpredictable step of nanotube opening. Further, the filling efficiency is too low to consider this method for large scale production. In addition, ferrous metals, which are of interest for magnetic applications, have high melting points (1565° C.) and can react with carbon.

U.S. Pat. No. 5,457,343 discloses nanometer sized carbon tubules enclosing a foreign material. The foreign material is introduced into the nanotube by forming an opening at the top portion of the carbon tubule either by contacting the foreign material with the top portion of the carbon tubule together with a heat treatment or by evaporation of the foreign material on the top portion of the carbon tubule together with heat treatment.

U.S. Pat. No. 5,543,378 discloses a carbon nanostructure having a palladium crystallite encapsulated therein.

U.S. Pat. No. 6,090,363 discloses a method for making carbon nanotubes open on at least one end by treating capped nanotubes with an oxidizing acid such as nitric acid. This patent also discloses methods for depositing materials into the carbon nanotubes once opened.

U.S. Pat. No. 6,129,901 discloses a method for producing uniform sized and uniformly aligned nanotubes and filling these nanotubes with metals using, for example electroless deposition.

Chemical vapor deposition (CVD) CNTs produced by template synthesis can be filled with water (Rossi et al. Nano Letters 2004 4:989-993; Naguib et al. Abstracts of Papers of the American Chemical Society Annual Meeting 2003 226: U535), ethylene glycol, hydrocarbons, and other liquids. Further, recent demonstration on a coulter-counter (Henriquez et al. Analyst 2004 129:478-482) shows that particulate flow inside nanotubes is possible.

SUMMARY OF THE INVENTION

An object of the present invention is to provide a method for producing carbon nanotubes loaded with functional nanoparticles which comprises synthesizing open carbon nanotubes and filling the open carbon nanotubes with a suspension of functional nanoparticles or a colloidal solution of functional nanoparticles. In one embodiment, the carbon nanotubes are synthesized by chemical vapor deposition of the carbon nanotubes onto an internal wall of a template. Carbon nanotubes are filled with the suspension of functional nanoparticles or colloidal solution of functional nanoparticle either before or after separation of the carbon nanotubes from the template.

Another object of the present invention is to provide a carbon nanotube loaded with functional nanoparticles. In one embodiment a magnetic carbon nanotube is provided comprising a hollow carbon nanotube filled with a suspension of magnetic nanoparticles. In this embodiment, the carbon nanotube is preferably filled with a ferrofluid. In other embodiments the hollow carbon nanotubes are filled with functional nanoparticles such as, but not limited to, colloidal gold nanoparticles and non-metallic diamond nanoparticles.

BRIEF DESCRIPTION OF THE FIGURES

FIG. 1(a) shows CNTs filled with ferrofluid in a magnetic field. Nanotubes are embedded in alumina.

FIG. 3(a) is a TEM image of part of a branched CNT, and FIG. (b) is a TEM Image of the CNTs with open ends, filled with magnetic particles from water based ferrofluid EMG 508. These images show that the nanoparticles are collected inside the CNT and form quite a dense structure. Attached to the walls of the CNT by adhesion forces, the particles stay intact after processing.

FIGS. 5(a) and (b) show magnetic CNTs oriented along in the plane of supporting wafer, $\mu_0 H=0.01$ Tesla.

FIG. 8(a) shows a fragment of CNT filled with non-metallic nanodiamonds. FIG. 8(b) shows a high resolution TEM image of a nanodiamond particle inside the nanotube. The spacing between layers of carbon equals to 0.206 nm, which is a characteristic distance for diamond lattice structure. The average size of nanodiamond particles is 5 nm.

DETAILED DESCRIPTION OF THE INVENTION

The present invention relates to methods for producing carbon nanotubes (CNTs) loaded with functional nanoparticles. In these methods, open CNTs are synthesized. Any method for synthesis of open CNTs can be used. An exemplary method is synthesis via chemical vapor deposition onto a template such as an alumina membrane. The open CNTs are then filled with a suspension of functional nanoparticles or a colloidal solution of functional nanoparticles. Because dragging of nanoparticles into nanotubes is mostly affected by the process of initial enforcement of the fluid body as a whole continuum (Kornev K. G. and Neimark, A. V. Journal of Colloid Interface Science 2003 262:253-262), it is expected that inertia-dominated flow will provide a useful means for filling the open CNTs. Once filled, the CNTs are sealed using various known methodologies. In one embodiment, the CNT tips are selectively sealed with polypirrol using bipolar electrochemistry (Bradley et al. Chemistry Preprint Archive 2003 3:245-250). Effects of functional nanoparticle separation in the filled nanotubes are expected to occur only at the late stage of penetration when quasi-stationary menisci have already formed (Karnis A. and Mason, S. G. Journal of Colloid and Interface Science 1967 23:120).

The methodologies described herein were used to produce CNTs loaded with functional magnetic nanoparticles. The resulting magnetic structures, also referred to herein as magnetic needles, are useful in numerous applications including but not limited to nanotechnology, memory devices and medicine.

As shown herein, the methodologies of the present invention provide a simple and versatile technique to produce magnetic tubes by filling CNTs with paramagnetic, iron oxide particles (approximately 10 nm in diameter). In this exemplary embodiment, commercial fluids were used to fill chemically vapor deposited CNTs with average outer diameter 300 nm. Examination of the filled nanotubes by transmission electron microscope (TEM) showed a high density of particles inside the CNT. Experiments using an external magnetic field demonstrated that almost 100% of the nanotubes became magnetic and could be easily manipulated in a magnetic field. These filled nanotubes can be used as nanosubmarines externally driven through blood vessels of a mammal by magnetic field and transporting nanoscale amounts of a drug or drugs from one point to the other. Also, these filled CNTs can be used in the form of nanowebs or films for magnetic recording or optical transducers for wearable electronics.

For these experiments, CNTs produced in accordance with methodologies set forth in Example 1 were used.

Figure 1:
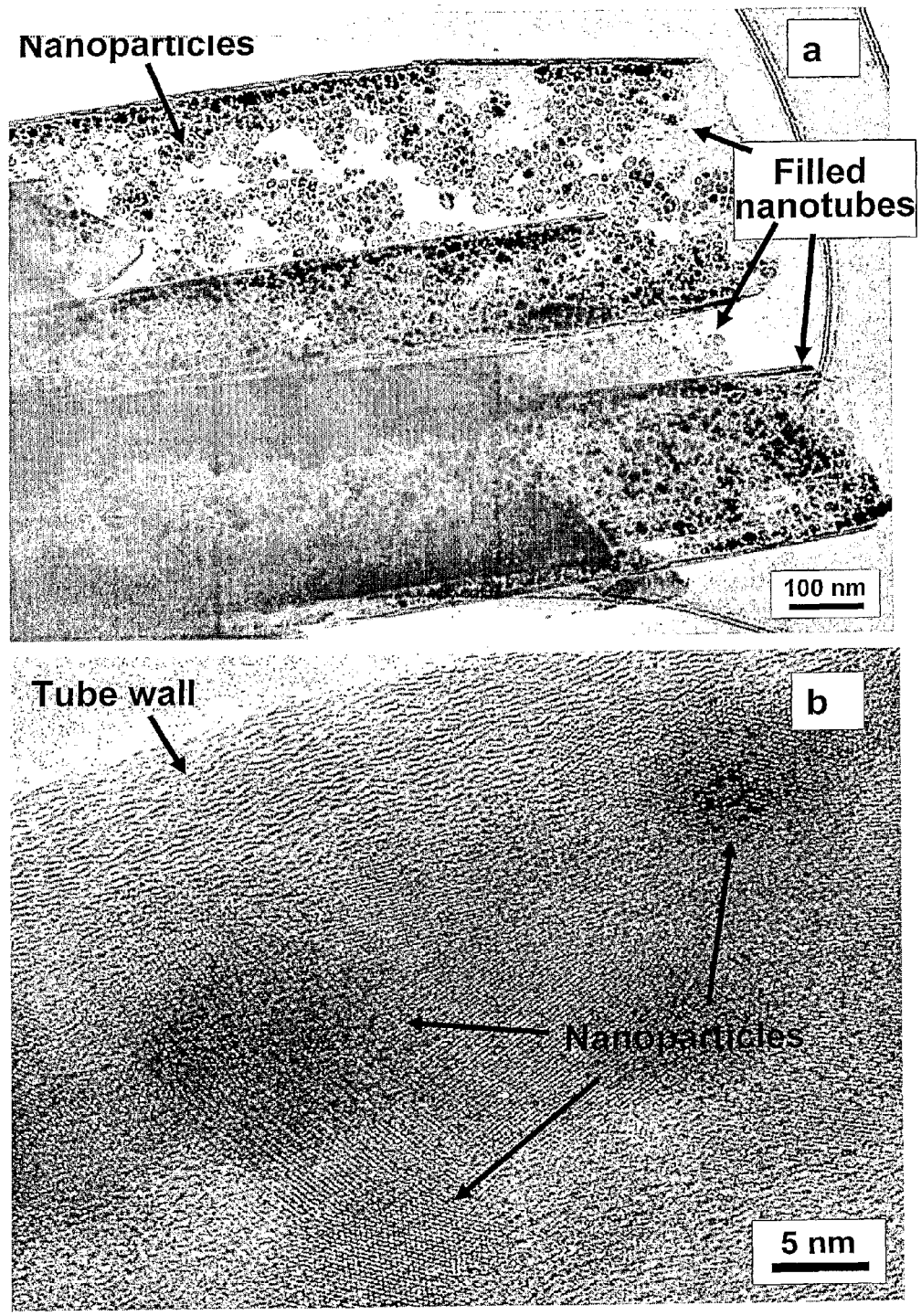
FIG. 1(a) and (b) are transmission electron microscope (TEM) images of CNTs filled with organic-based ferrofluid EMG 911.
FIG. 1(b) is a high resolution TEM image of a fragment of a filled nanotube, without magnetic field. The particles are agglomerated inside the nanotube.
Figure 2:
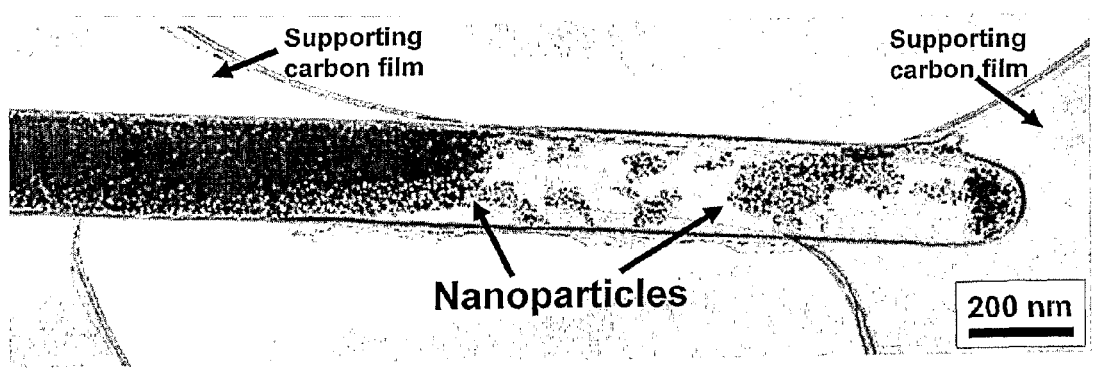
FIG. 2 is a TEM image of a filled tube without magnetic field. The closed tip of the nanotube shown is revealed after dissolution of the aluminum template in NaOH followed by sonicating, filtering, and rinsing in an alcohol. This image shows high density of particles inside the nanotube even after several hours of processing.

In one embodiment, the CNTs were filled with magnetic particles via filling of the alumina membrane upon which the CNTs were deposited. Upon deposition of a droplet of ferrofluid onto the membrane, the fluid invaded the pores. A magnetic field was applied to control the magnetic anisotropy of prepared magnetic peapods. A permanent magnet H of approximately 4 kGauss was mounted underneath the membrane. Even without field the penetration happened almost instantaneously. Applied magnetic field increased the rate of penetration, because it created an additional force to direct magnetic nanoparticles towards the magnet, i.e. into the tubes. After evaporation of the carrying liquid at room temperature, the membrane was broken into tiny pieces and dispersed in isopropanol for TEM examination. During the processing, the magnetic grains deposited outside the nanotubes were washed out, while the grains deposited inside, were held by adhesion forces. In FIG. 1, TEM micrographs show the typical packing morphology of magnetic grains inside the nanotubes. A detailed TEM analysis showed that nanoparticles fill the nanotubes equally with and without magnetic field thus indicating that filling is driven by capillary forces.

Figure 3:
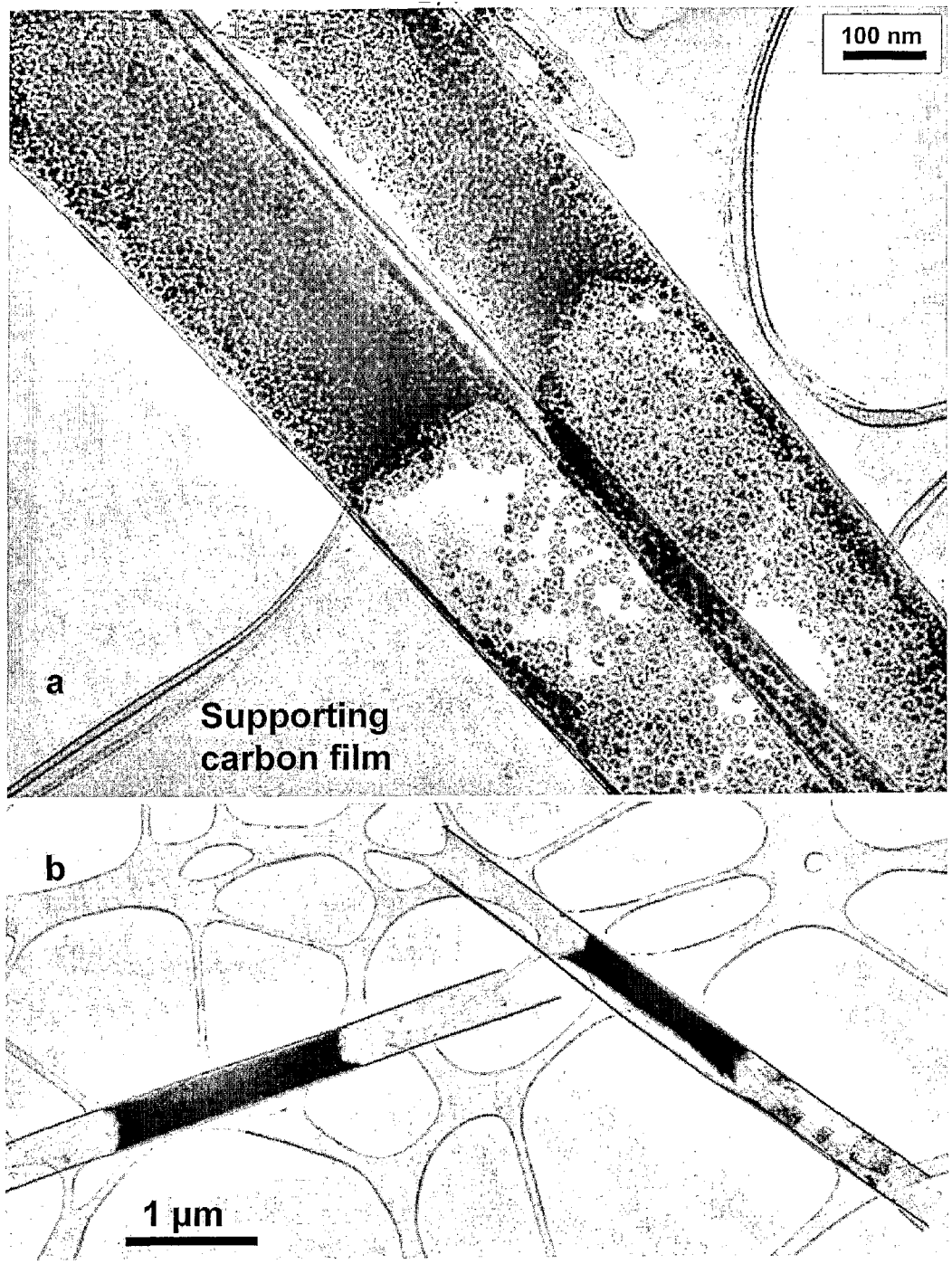
FIGS. 3(a) and (b) show the process of filling of individual nanotubes.
Figure 4:
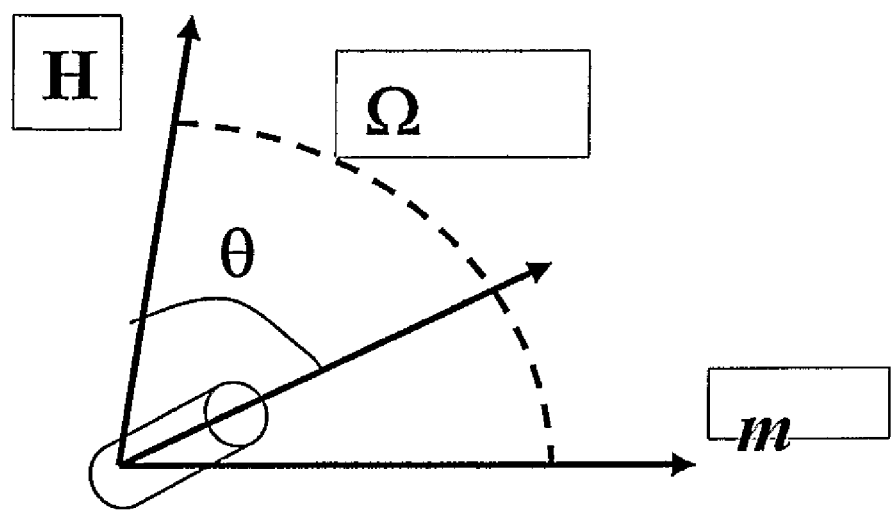
FIG. 4 is a schematic of orientation of magnetic moment m and magnetic field H in a rotating CNT.

In another embodiment, individual nanotubes were filled with magnetic nanoparticles. Using this technique, the alumina template after preparation of the CNTs by the CVD method was dissolved in 4.0 M NaOH. After sonication, the solution was vacuum filtered through the Polyester nucleopore membrane (Osmonic Corp.) with the pore size of 0.2 µm. Then the filtrate was dispersed in toluene. A few milliliters of this filtrate solution of CNTs dispersed in toluene were then filtered again using a similar Polyester membrane. After filtration, the residue was rinsed with alcohol and distilled water, and then dried. Typically, a gray area of concentrated nanotubes appeared on the substrate after drying. A drop of ferrofluid was deposited on that gray spot. Again, after complete evaporation of the solvent, the substrate was rinsed with the alcohol, immersed into a small vial and 5 ml of alcohol was added. The vial was put into a sonicator and the deposit was removed from the membrane. This solution was analyzed by TEM. TEM images are depicted in FIGS. 3 and 4.

Figure 5A:
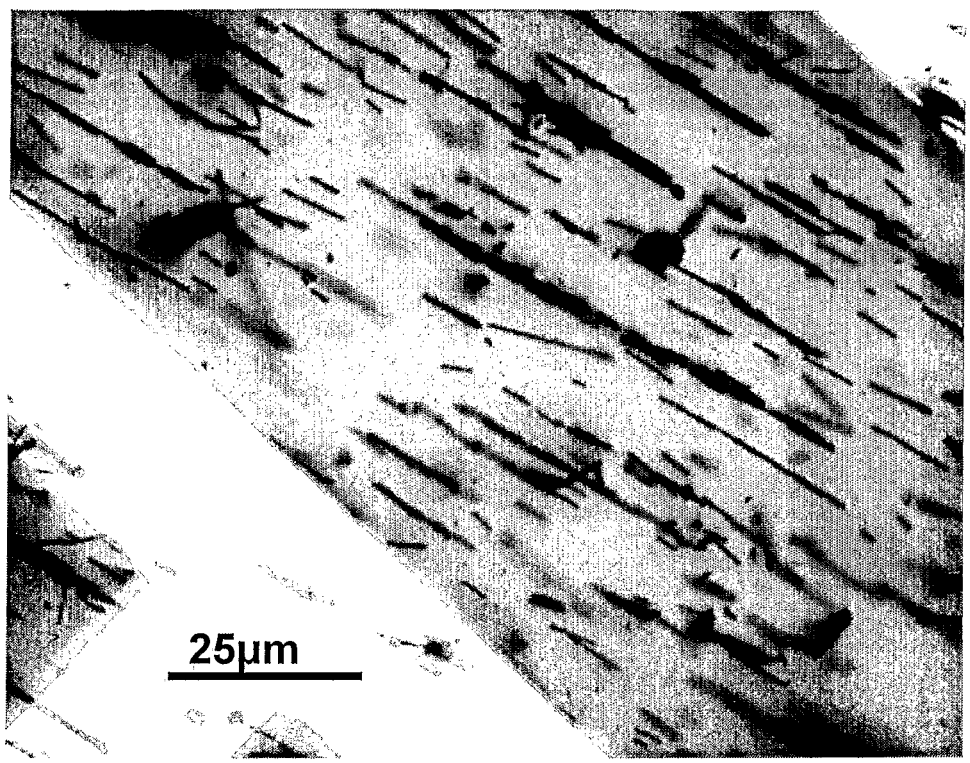
FIGS. 5(a), (b) and (c) show manipulation of magnetic nanotubes by magnetic field.
Figure 5B:
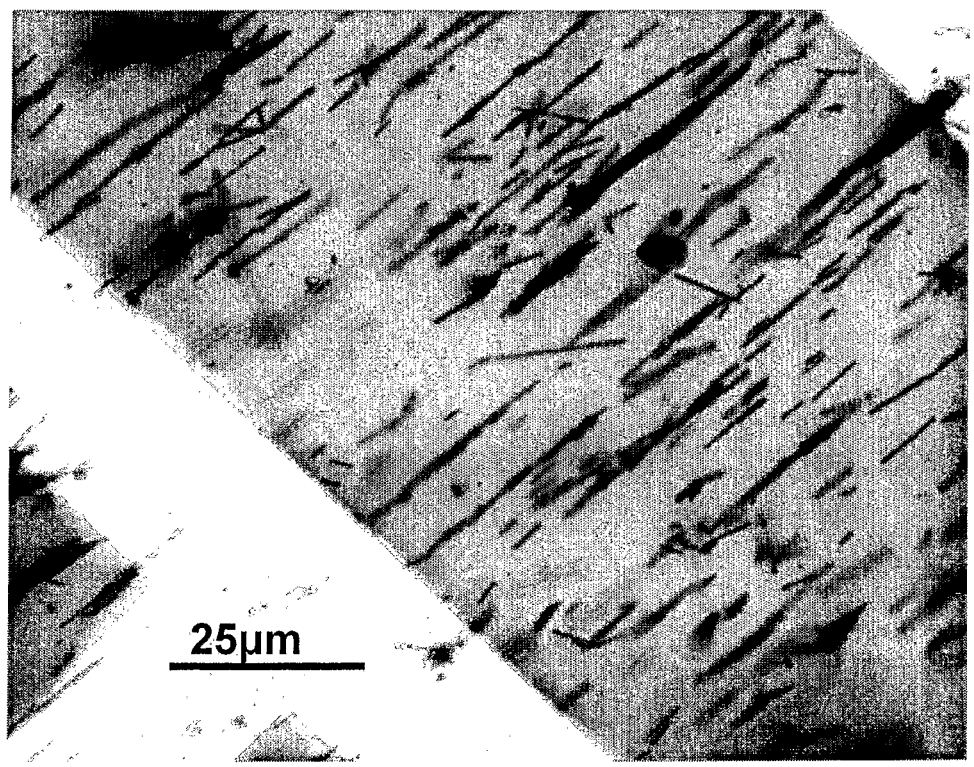
FIG. 5(c) shows magnetic nanotubes frozen in applied magnetic field perpendicular to the wafer $\mu_0 H=0.03$ Tesla.
Figure 5C:
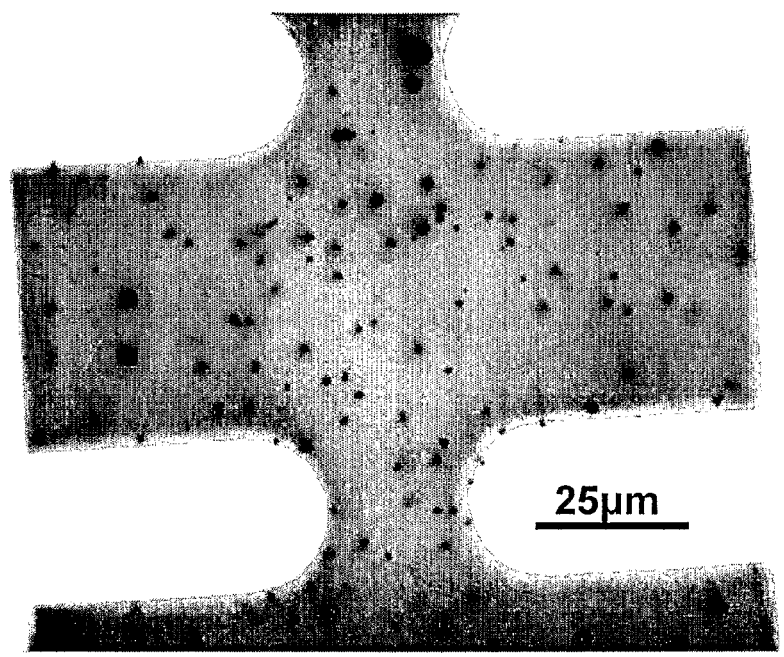
Figure 6:
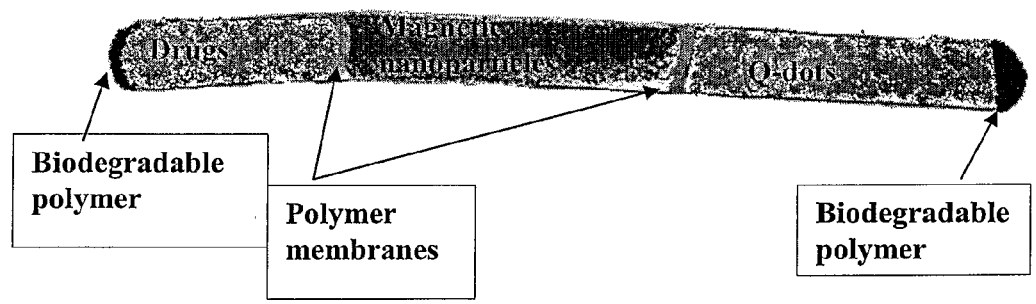
FIG. 6 provides an example of a magnetically driven nanosubmarine based on CNT with encapsulated magnetic particles, drugs or quantum dots (QDs). QDs allow for optical control of the position of nanosubmarines. Drugs can be delivered to the timorous region and released upon polymer biodegradation.

As shown by the TEM images, filling of the nanotubes either via the alumina membrane or individually gives almost the same results with the nanotubes being filled with magnetic nanoparticles. The density of magnetic grains was so high that the grains can be probed by rough macroscopic technique. In particular, the alumina membranes filled with magnetic grains can be easily dragged by permanent magnet after drying. Suspended in liquids, magnetic nanotubes follow the change of the direction of applied magnetic field. FIG. 5 shows typical behavior of suspension of magnetic nanotubes placed in magnetic field of $\mu_0 H$=0.01 Tesla, where $\mu_0$ is permeability of vacuum. Magnetic nanotubes can be oriented in the plane of silicon wafer with golden islands (see FIGS. 5($a$) and ($b$)), or can be forced to freeze perpendicularly to the wafer (see FIG. 5($c$)). In the field, the nanotubes form long chains with the lengths greater than the width of the golden islands, 25 μm. As seen from that panel, all nanotubes are sensitive to application of magnetic field. In particular, all nanotubes seen in the spot of camera stay perpendicular with respect to the wafer, FIG. 5$c$. This demonstrates a yield of 100% magnetic nanotubes after filling.

An analysis of magnetization of magnetic nanotubes within membranes is extremely difficult. This is because an incremental increase of the weight of membranes after filling is so small that available balances cannot resolve the distinction. Also, even after rinsing the membrane, some particles are left at the membrane surfaces. Estimates based on an experimental magnetization curve taken on membranes, however, show that magnetic particles on the membrane surface contribute significantly to the magnetization. Thus, rotation field experiments were used to estimate the magnetization parameters of individual CNTs. In rotating magnetic field, the CNTs filled with magnetic particles follow the field and rotate. However, the magnetic moment coupling with the field cannot be considered as a sum of each individual magnetic grain, because collected together within the nanotube, magnetic particles constitute a multidomain magnetic nanotube. Upon application of magnetic field, magnetic moments of each magnetic particle rotate to follow the local magnetic field. This local field is influenced by the neighbors in a complicated way. Unlike typical magnetic solids, in which motion of magnetic spins can be, in a first approximation, considered independently of the deformations of the atomic lattice, in filled nanotubes rotations of magnetic moments and particles both are interconnected. To the best of the inventors' knowledge, the problem of magnetization of granular materials such as these has never been considered in the literature. This makes an estimate of magnetic properties of CNTs challenging. However, an estimate of an effective magnetization associated with the magnetic moments oriented along the nanotube can be made.

With respect to the stationary reference frame, the angle between the direction of the external field H and the reference axis X changes with time as $\Omega=\omega t$. If the angle between the nanotube axis, which is supposed to be the axis of magnetization m, and the direction of the field is θ, the following equation of tube rotation (Landau, L. D. and Lifshitz, E. M. Electrodynamics of continuous media (Pergamon, Oxford 1960)) can be written:

$$\gamma(\omega-\theta')=\mu m H \sin\theta \quad (1)$$

where prime denotes the time derivative, and γ is the friction coefficient of the tube (Doi, M. and Edwards, S. F. The theory of polymer dynamics Oxford University Press, London 1986), $$\gamma=\pi\eta L^3/3\ ln(L/d)-3A), A \sim 0.8. \quad (2)$$

Here L is the tube length, d is the tube external diameter, and η is the fluid viscosity. As seen from Eq. (1), there is a solution θ=constant, which disappears as the frequency of the field becomes:

$$\omega_{cr}=\mu_0 mH/\gamma.$$

Because of the scatter in the tube length, different CNTs stop spinning at different frequencies. Experiments were performed with water-based suspension on CNTs in the field of 0.007 Tesla. The critical frequency varies between $f_{cr}$=6-10 Hz. Taking these values, the magnetization is estimated through the formula $$m=\omega_{cr}\gamma/\mu_0 H=2\pi f_{cr}\pi\eta L^3[(3\ ln(L/d)-2.4)\mu_0 H]^{-1}$$

where L=10-15 μm, d=300 nm and $\mu_0$ H=0.007 Tesla. The experimental data give m=$5\times10^{-15}$–$2\times10^{-14}$ A·m². If the saturation magnetization of magnetite is $M_s$=4.46×10$^5$ A/m (Rosensweig, R. E. Ferrodynamics (Cambridge University Press, Cambridge 1985), then the magnetic moment of individual magnetic grain is $m_g=\pi M_s d_g^3/6$=2×10$^{-19}$ A·m². Assuming the packing factor is 0.74, the number of magnetic grains in the tubes is estimated as N~3×10$^4$-10$^5$.

The high magnetization of the loaded CNTs of the present invention, as well as the compatibility of CNTs to many polymeric materials, makes these magnetic nanotubes produced in accordance with the present invention highly attractive engineering materials for multiple uses. For example, functionally nanoparticle loaded CNTs can be used as nano-submarines for drug delivery in desired locations in the body, as well as for diagnostics without surgical interference. Further, experiments shown in FIG. 5($c$) suggest use of these magnetic nanotubes instead of nanoposts in fluidic chips for DNA separation (Bakajin et al. Analytical Chemistry 2001 73:6053-6056; Cao et al. Applied Physics Letters 2002 81:3058-3060). That is, one can apply magnetic field to freeze nanotubes and to vary the intertube spacing in order to unravel DNA coils and separate them in a prescribed manner following, for example, Bakajin et al. (Analytical Chemistry 2001 73:6053-6056), Cao et al. (Applied Physics Letters 2002 81:3058-3060), Doyle et al. (Science 2002 295:2237) and Minc et al. (Analytical Chemistry 2004 76:3770-3776). The list of applications of magnetic nanotubes can be extended to include, but is in no way limited to, materials for wearable electronics (Wu et al. Science 2004 305:1273-1276; Zrinyi et al. Polymer Gels and Networks 1998 6:441-454; and Nikitin et al. Polymer Science Series A 2004 46:301-309), cantilever tips in magnetic force microscopes (Yoshida et al. Physica B-Condensed Matter 2002 323:149-150), magnetic stirrers in microfluidic devices, and magnetic valves in nanofluidic devices (Brochard, F. and DeGennes, P. G. Journal de Physique 1970 31:691-708). Thus, the versatile technique of the present invention provides a means for nanoengineering of complex multifunctional nanomachines. Other particulate fluids, e.g. solutions of quantum dots, can be used as well. In previous studies, water (Rossi et al. Nano Letters 2004 4:989-993; Naguib et al. Abstracts of Papers of the American Chemical Society, Annual meeting 2003 226:U535) as well as a number of organic fluids including glycerin, alcohols, benzene, and cyclohexane were demonstrated to be encapsulated into the same kind of nanotubes. Thus, these liquids, as well as other liquids with similar characteristics can be used in accordance with the present invention as the carriers for other functional particulates and emulsion systems or biopolymer solutions for nanotube filling.

Figure 7:
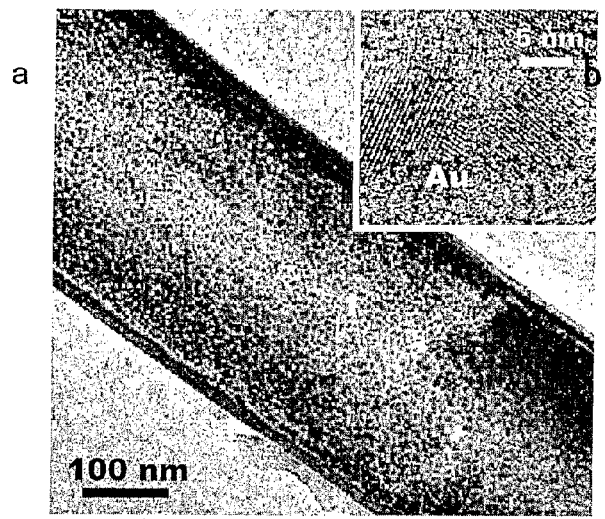
FIG. 7 is a TEM image of CNT filled with colloidal gold nanoparticles. The inset shows high resolution TEM image of the gold nanoparticles inside the nanotube. Average size of gold nanoparticles is 10 nm.
Figure 8:
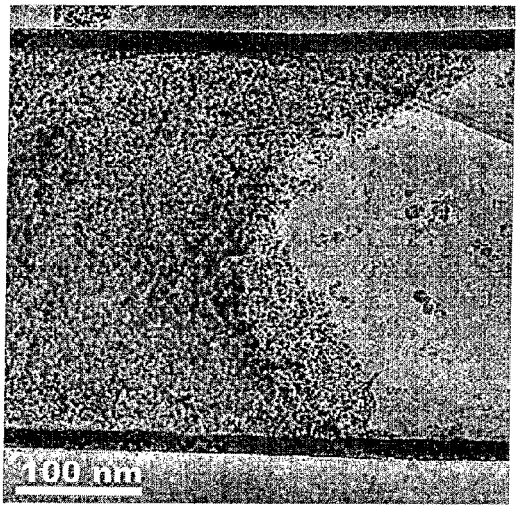
FIGS. 8(a) and 8(b) are TEM images of CNTs filled with nanodiamond particles.
Figure 8B:
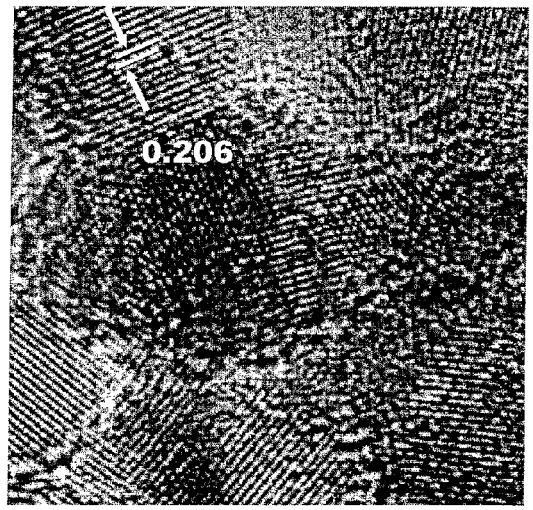

As will be understood by the skilled artisan upon reading this disclosure, other particulate fluids, emulsions, and polymer solutions can be used to fill hollow CNTs in accordance with the present invention and transform them into multifunctional nanostructures. For example, the methods described herein where used to functionally fill hallow CNTs with gold colloidal nanoparticles (see FIG. 7). Gold (Au) nanoparticles inside carbon nanotubes can induce localized plasmon resonance and be used in surface-enhanced Raman, enabling recording of Raman spectra from contents of a single nanopipe, or from biological molecules attached to the nanotube. These same technique were also used to fill hollow CNTs with non metallic nanoparticles, in particular with nano diamonds (see FIG. 8).

As shown herein, the present invention provides a relatively easy, inexpensive and fast method of filling CNTs with functional nanoparticles, and in particular magnetic nanograins, colloidal gold nanoparticles as well as nonmetallic nanodiamond particles. Based on the phenomenon of spontaneous penetration of wetting fluids into capillaries, this technique opens doors in engineering magnetic nanotubes. The magnetization of magnetic CNTs is controlled by the amount of encapsulated nanograins, thus making it very high. In these experiments, for example, the number of magnetic grains in the tubes varied between $10^4$ and $10^5$. Further, the yield of magnetic nanotubes after wet filling was sufficiently high, tending to be 100%. As evidence of this, FIG. 5 shows typical behavior of magnetic nanotubes in applied magnetic field. The vast majority of nanotubes follow the field, thus manifesting their magnetic nature. Controllable manipulation of magnetic nanotubes with micromagnetic points provides a straightforward way for utilization of these magnetic nanoneedles in different nanofluidic and electronic devices. Au nanoparticles inside the carbon nanotubes can induce localized plasmon resonance and be used in surface-enhanced Raman spectroscopy, enabling recording of Raman spectra from contents of a single nanopipe. Other particulate fluids, emulsions, and polymer solutions can be used to fill nanotubes and transform them into multifunctional nanostructures. As an example, hollow CNTs were filled with non-metallic nanodiamond particles (see FIG. 8).

The following nonlimiting examples are provided to further illustrate the present invention.

EXAMPLES

Example 1

Synthesis of CNTs

All experiments were performed with carbon nanotubes produced by the chemical vapor deposition (CVD) technique. The nanotubes were formed in the straight cylindrical pores connecting both faces of a template comprising an alumina membrane. The alumina membrane template comprised an Anodisc of 13 mm in diameter purchased from WhatmanR. The pore diameter and thickness of the membrane determine the dimensions of the nanotubes. For experiments described herein, the pore size was 300 nm on average, and the membrane thickness was 60 µm. The synthesis of CNT by CVD is described in detail by Bradley et al. (Chemistry Preprint Archive 2002 237-242). The resulting CNTs have open ends from one or both sides, and their walls are highly disordered and hydrophilic to allow water to invade the tubes (Rossi et al. Nano Letters 2004 4:989-993; Naguib et al. Abstract of Papers of the American Chemical Society, Annual meeting 2003 226:U535; Ye et al. Nanotechnology 2004 15:232-236). This makes it possible to fill the nanotubes not only with organic based ferrofluids but with water-based ferrofluids as well. CNTs were filled with magnetic particles using the following commercially available ferrofluids: water based (EMG 508) and organic based (EMG 911) (Ferrotec Corporation) which carry the magnetite particles ($Fe_3O_4$) with the characteristic grain size of 10 nm. Samples were characterized by transmission electron microscopy (TEM) using a JEOL JEM-2010F (200 kV) with a point-to-point resolution of 0.23 nm. The TEM samples were prepared by dispersing the nanotubes in isopropanol and then placing them onto a copper grid coated with a lacy carbon film. Images of nanotubes in experiments with external magnetic field of strength 110-120 Gauss were taken on a Leca DM LFS microscope with a Leica HCX APO 63×/0.90 U-V-I water immersion lens and MagnaFire SP Model S99805 camera.

What is claimed is:

1. A method for producing carbon nanotubes loaded with functional nanoparticles comprising:
    synthesizing oriented open carbon nanotubes onto an internal wall of a porous membrane template such that the internal walls of the carbon nanotubes are disordered, or hydrophilic, or both disordered and hydrophilic; and
    filling the open carbon nanotubes with a suspension or colloidal solution of at least one type of functional nanoparticles wherein at least one type of functional nanoparticles attaches to the walls of the carbon nanotubes by adhesion forces.

2. The method of claim 1 wherein the open carbon nanotubes are synthesized by chemical vapor deposition.

3. The method of claim 1 wherein the synthesized carbon nanotubes are separated from the template before filling the carbon nanotubes with the a suspension of functional nanoparticles or a colloidal solution of functional nanoparticles.

4. The method of claim 1 wherein the synthesized carbon nanotubes are separated from the template after filling the carbon nanotubes with the a suspension of functional nanoparticles or a colloidal solution of functional nanoparticles.

5. The method of claim 1 wherein the template comprises an alumina membrane.

6. The method of claim 1 wherein the suspension of functional nanoparticles comprises a ferrofluid.

7. The method of claim 1 further comprising the application of an external magnetic field.

8. The method of claim 2 further comprising the application of an external magnetic field.

* * * * *